United States Patent
Di Emidio

(10) Patent No.: US 6,821,279 B2
(45) Date of Patent: Nov. 23, 2004

(54) ANTI-TRAUMA SURGICAL PLATE USED TO FIX MANDIBULAR STUMPS

(75) Inventor: Paolo Di Emidio, Controguerra (IT)

(73) Assignee: Piergiacomi Sud-S.R.L., Monteprandone (IT)

( * ) Notice: Subject to any disclaimer, the term of this patent is extended or adjusted under 35 U.S.C. 154(b) by 370 days.

(21) Appl. No.: 10/035,053

(22) Filed: Dec. 28, 2001

(65) Prior Publication Data

US 2002/0193796 A1 Dec. 19, 2002

(30) Foreign Application Priority Data

Jun. 15, 2001 (IT) .................................. MC20010029 U

(51) Int. Cl.⁷ .............................................. A61B 17/58
(52) U.S. Cl. ..................................... 606/69; 623/17.17
(58) Field of Search ...................... 606/69, 61, 71–73, 606/54; 623/17.17, 17.18, 17.19, 17.15, 23.41; 433/173, 174

(56) References Cited

U.S. PATENT DOCUMENTS

| | | | | | |
|---|---|---|---|---|---|
| 3,488,779 | A | * | 1/1970 | Christensen | 623/16.11 |
| 5,554,194 | A | * | 9/1996 | Sanders | 623/17.17 |
| 6,060,641 | A | * | 5/2000 | Manolidis | 128/898 |
| 6,296,644 | B1 | * | 10/2001 | Saurat et al. | 606/61 |
| 2003/0108845 | A1 | * | 6/2003 | Givannone et al. | 433/173 |

FOREIGN PATENT DOCUMENTS

JP 2001-29113 * 2/2001 ........... A44C/25/00

* cited by examiner

Primary Examiner—David O. Reip
Assistant Examiner—D. Jacob Davis

(57) ABSTRACT

The present invention relates to an anti-trauma surgical plate used to fix mandibular stumps that comprises two lateral series of rings alternated with ribbon-like connection plates and with an intermediate series of balls joined with cylindrical arms.

2 Claims, 1 Drawing Sheet

ANTI-TRAUMA SURGICAL PLATE USED TO FIX MANDIBULAR STUMPS

BACKGROUND OF THE INVENTION

The present patent application relates to a surgical plate used to fix mandibular stumps.

To better illustrate the advantages of the artefact according to the present invention, the state-of-the-art of the sector technique with typical drawbacks must be described.

A particularly aggressive form of cancer is represented by epidermoid carcinoma located in the oral cavity.

If case of late diagnosis, this cancer originates lymph node metastasis and mandibular infiltration.

In the presence of neoblastic mandibular infiltration, the most typical intervention is represented by the resection of the infiltrated bone segment.

Apart from complying with a series of parameters to guarantee oncological efficiency, surgery must provide for the immediate anatomical and function reconstruction of the resected part, through the stable mutual fixing of the mandibular stumps.

Today this need is satisfied by means of steel or titanium plates basically composed of a sort of "chain" of rings connected with ribbon-like rectangular plates; it being provided that each end of the plate is fixed on the outside of the bone stump in order to restore the continuity and stability of the entire mandibular section affected by bone resection.

In particular, the two ends of the plate are fixed to the bone stumps by means of suitable screws that pass through the rings of the plate and firmly engage in the mandibular bone stumps.

Based on experience, traditional plates are valid from the anatomical function viewpoint, although they have a serious drawback, that is the fact that a few months after their application, they tend to incise the internal oral mucosa and the cheek.

More precisely, the incision of the oral cavity is caused by the central section of the plate, that is the section that occupies the free space created after the surgical removal of the bone part with cancer infiltration, which remains "suspended" with no support between the stumps.

In the worst cases the plate may even appear on the surface, after incising the cheek from part to part, like a blade.

This phenomenon, defined as "superficialisation", is typical of traditional plates and mainly due to the flat sharp-edged shape of the plate that, due to the continuous inevitable interference with contiguous areas in the oral cavity, results in the local trauma illustrated above.

SUMMARY OF THE INVENTION

The plate according to the present invention has been developed in order to avoid the aforementioned problem. In other words, it ensures the same functionality of traditional plates and eliminates the serious drawback illustrated above affecting the user's oral cavity.

The two ends of the new plate comprise a series of rings, joined with ribbon-like plates, regularly alternated with the rings; it being provided that the two series of rings are connected with an intermediate series of balls joined by regularly alternated cylindrical arms.

The two lateral series of rings can be advantageously used to fix the ends of the plate to the two mandibular stumps. In practical terms, fixing can be obtained by screws that are inserted in the ring holes and engaged in the external mandibular corticalis.

The intermediate series of balls is designed to be placed longitudinally in intermediate position between the two stumps, replacing the bone section that was removed surgically.

It can be easily understood that the interference created by the plate with the oral cavity is necessarily located in the intermediate area of the plate (that is the series of balls alternated with cylindrical arms) that has no sharp edges and therefore is not capable of creating incisions or damages for the user.

BRIEF DESCRIPTION OF THE DRAWINGS

For major clarity the description of the invention continues with reference to the enclosed drawing, which is intended for purposes of illustration and not in a limiting sense, whereby.

DESCRIPTION OF THE INVENTION

With reference to this FIGURE, the two ends of the plate are provided with two series of rings (1) connected with regularly alternated ribbon-like plates (1a).

As mentioned earlier, the rings (1) are fixed edgeways to the mandibular stumps (M, M') with traditional screws (V).

The two series of rings (1) are joined with an intermediate series of balls (2) regularly alternated with cylindrical connection arms (2a).

Figure 1:
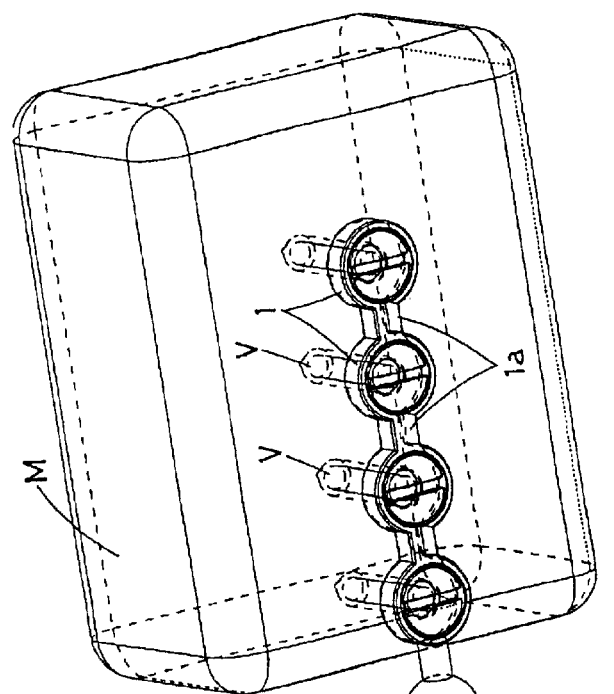
FIG. 1 is an axonometric view of the plate in its operating position between two mandibular stumps shown as two cubes (M, M').
Figure 1:
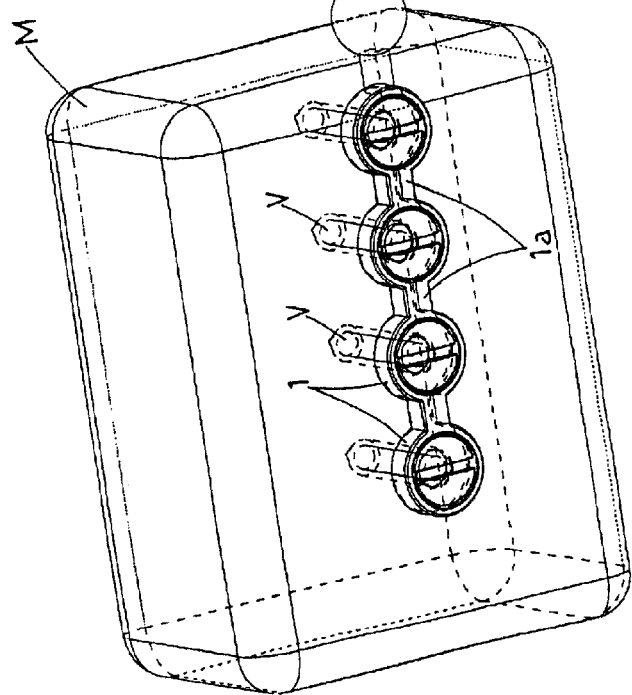

FIG. 1 clearly shows that the intermediate series of balls (2) is designed to occupy the entire space between the two mandibular stumps (M, M'); it can be said that the balls (2) together with the cylindrical connection arms (2a) are the only parts that may come into contact with the oral mucosa and the cheek.

In view of the fact that the balls (2) and the arms (2a) have a rounded surface, it appears evident that the continuous interference between these parts of the plate and the user's mouth cannot create any type of trauma.

What is claimed is:

1. An anti-trauma surgical plate characterised by the fact that it comprises two lateral series of rings (1) capable of receiving screws (V) alternated with ribbon-like connection plates (1a) and with an intermediate series of balls (2) joined with cylindrical arms (2a), each of the series of rings alternating with two or more of the connection plates.

2. An anti-trauma surgical device to be joined to bone in a human patient, the device comprising:
   a first end and an opposite second end, each end having a series of rings,
   the rings in each series are joined by a series of ribbon-like plates which alternate with the respective rings,
   each of the rings has a ring hole into which a respective screw is disposed, the screws being adapted to be anchored in the bone of the patient,
   the rings on the first end are connected to the rings on the second end by an intermediate series of spaced-apart balls,
   cylindrical connecting arms being disposed alternating with the spaced-apart balls.

* * * * *